(12) United States Patent
Marche et al.

(10) Patent No.: US 9,138,959 B2
(45) Date of Patent: Sep. 22, 2015

(54) RESILIENT LAMINATE HAVING INCREASED STRENGTH AGAINST STRESSES

(75) Inventors: Thierry Marche, La Chapelle Basse Mer (FR); Nathalie Moinard, Nantes (FR)

(73) Assignee: APLIX, Paris (FR)

( * ) Notice: Subject to any disclaimer, the term of this patent is extended or adjusted under 35 U.S.C. 154(b) by 254 days.

(21) Appl. No.: 13/824,439

(22) PCT Filed: Sep. 2, 2011

(86) PCT No.: PCT/FR2011/000487
§ 371 (c)(1),
(2), (4) Date: Mar. 18, 2013

(87) PCT Pub. No.: WO2012/038613
PCT Pub. Date: Mar. 29, 2012

(65) Prior Publication Data
US 2013/0177741 A1      Jul. 11, 2013

(30) Foreign Application Priority Data

Sep. 23, 2010 (FR) ...................................... 10 03776

(51) Int. Cl.
*B32B 3/26*   (2006.01)
*B32B 5/04*   (2006.01)
(Continued)

(52) U.S. Cl.
CPC ............. *B32B 3/263* (2013.01); *A61F 13/4902* (2013.01); *B32B 5/04* (2013.01);
(Continued)

(58) Field of Classification Search
CPC ........ B32B 3/263; B32B 5/145; B32B 5/142; B32B 5/04; B32B 27/12; B32B 2555/02; B32B 2307/51; A61F 13/4902; A61F 13/5633; A61F 13/5638; A61F 13/5644; A61F 13/622; A61F 13/62; A61F 2013/49022; Y10T 428/24521

USPC .......................................................... 428/161
See application file for complete search history.

(56) References Cited

U.S. PATENT DOCUMENTS 6,221,483 B1   4/2001   Hilston et al.
6,245,401 B1   6/2001   Ying et al.
(Continued)

FOREIGN PATENT DOCUMENTS

JP          6-293067        10/1994

OTHER PUBLICATIONS

English translation of JP06293067 to Arakawa, Oct. 1994.*
(Continued)

*Primary Examiner* — Aaron Austin
*Assistant Examiner* — Jasper Saberi
(74) *Attorney, Agent, or Firm* — Renner, Kenner, Greive, Bobak, Taylor & Weber

(57) ABSTRACT

The invention relates to a resilient laminate comprising, in a vertical direction, a stack of at least one nonwoven layer and a ply consisting of a part or integral part attached to the at least one nonwoven layer, in particular by means of an adhesive such as glue, the ply comprising at least one resilient film area and at least one so-called rigid film area made of a material that is less resilient than the material of the resilient area, in particular an area made of a non-resilient material, the ply being produced by the coextrusion of the at least one resilient film and the at least one rigid film, such that an interface is formed therebetween, characterized in that, from a cross-sectional view, the curve or line formed by the interface between the two films comprises at least one first substantially rectilinear segment, and at least one second substantially rectilinear segment which is angled relative to the at least one first segment. The curve or line formed by the interface between the two films extends from a point (P0) on the lower face of the laminate to a point (P1) on the upper face of the laminate, said points being horizontally offset in relation to one another and the diagonal line passing through said two points being inclined in relation to the vertical to the laminate.

10 Claims, 7 Drawing Sheets

(51) Int. Cl.
  *B32B 27/12* (2006.01)
  *B32B 5/14* (2006.01)
  *A61F 13/49* (2006.01)

(52) U.S. Cl.
  CPC ............... *B32B 5/142* (2013.01); *B32B 5/145* (2013.01); *B32B 27/12* (2013.01); *A61F 2013/49022* (2013.01); *B32B 2307/50* (2013.01); *B32B 2307/51* (2013.01); *B32B 2535/00* (2013.01); *B32B 2555/02* (2013.01); *Y10T 428/24521* (2015.01)

(56) References Cited

U.S. PATENT DOCUMENTS

2005/0060849 A1   3/2005   Vanbenschoten et al.
2007/0154683 A1   7/2007   Ausen et al.

OTHER PUBLICATIONS

Database WPI (Week 199502, Thomson Scientific, London, GB; AN 1995-009314 XP002641187) (2 pages—dated Jun. 14, 2011 09:14:18).

* cited by examiner

RESILIENT LAMINATE HAVING INCREASED STRENGTH AGAINST STRESSES

The present invention relates to a laminate comprising at least one elastic film, fixed in particular by means of adhesive, in particular glue, to at least one non-woven layer, and in particular two non-woven layers, an upper and a lower layer respectively. This type of laminate is used in particular in applications in the field of clothing, in particular disposable clothing, such as nappies and incontinence pads for adults, or in the medical field in the form of an elastic bandage. In nappies the laminates are used in the area forming a waistband around the waist of babies. In a particularly advantageous application in nappies the laminates are used to form elastic tabs which ensure that the nappy is secured in place on the baby, in particular in an elastic manner, the tab having for example the male elements of an grip fastening, in particular hooks, designed for example to cooperate with loops on a central part of the waistband of the nappy.

Laminates of the type mentioned above are already known from many different documents of the prior art. It would be desirable to provide laminates of this type that can be produced in the simplest possible manner, in particular adapted for large scale production and which are also highly resistant over time to the stresses that they may be subjected to during their use, in particular as part of the production of a nappy.

According to the invention, the laminate comprises a stack, in a vertical direction, of at least one non-woven layer and a layer made in one part or as an integral part attached to the at least one non-woven layer, in particular by means of an adhesive such as glue, the layer comprising a first face or lower face and a second face or upper face between which at least one elastic section in the form of a film extends and at least one rigid section in the form of a film made from a less elastic material than the material of the elastic section, in particular a section made from a non-elastic material, the layer being obtained by coextrusion of the at least two elastic and rigid films, such that an interface is formed between them, characterised in that, as viewed in cross section, the curve or line formed by the interface between the two films extends from a point (P0) on the lower face to a point (P1) on the upper face mutually offset in horizontal direction, the diagonal line passing through these two points being inclined in relation to the vertical of the layer;

the peak point (P) of the curve on the side of the rigid film is defined as the point most remote from the diagonal line from the side of the rigid film, the distance from the diagonal line being measured perpendicular to the latter, the peak point being merged with the point of the lower face in cases where the curve does not exceed the diagonal from the side of the rigid film, and the hollow point (P2) of the curve from the side of the elastic film is defined as being the point that is most remote from the diagonal line from the side of the elastic film, the distance to the diagonal line being measure perpendicular to the latter, the hollow point being merged with the point on the upper face in cases where the curve does not exceed the diagonal from the side of the elastic film;

at least one of the peak and hollow points being different respectively from the lower and upper points;

the line passing through the point of the lower face and the peak point and/or the line passing through the point of the upper face and the hollow point form an angle with the line passing through the hollow point and the peak point; and at least one out of the line (P0P) lower point-peak point, line (PP2) peak point-hollow point and line (P2P1) hollow point-upper point is inclined respectively in relation to the vertical direction, in relation to the horizontal direction and in relation to the vertical direction.

According to a first embodiment the hollow point is merged with the upper point and the lower point is different from the peak point.

According to a second embodiment, the peak point is merged with the lower point and the upper point is different from the hollow point.

According to a third embodiment, the peak point is different from the lower point and the upper point is different from the hollow point.

According to one embodiment the lower point and the peak point are different, the line lower point-peak point is inclined in relation to the vertical and the line hollow point-peak point is substantially horizontal.

According to another embodiment, the lower point and the peak point are distinct from one another, the line lower point-peak point is substantially vertical and the line peak point-hollow point is inclined in relation to the horizontal.

According to another embodiment the lower point and the peak point are different, the line lower point-peak point is inclined in relation to the vertical and the line peak point-hollow point is inclined in relation to the horizontal.

According to a particularly preferred embodiment the curve comprises between the lower face and the peak point a lower segment that is substantially straight and in particular is straight.

In particular, the curve comprises a lower segment that is substantially straight, in particular is straight, which extends from the lower face to the peak point.

According to a particularly preferred embodiment the curve has a substantially straight intermediate segment, in particular straight, between the peak point and the hollow point In particular, the curve has an intermediate segment which extends from the peak point to the hollow point.

Preferably, the extension in the horizontal direction of the line lower point-peak point is smaller than the extension in horizontal direction of the line peak point-hollow point.

According to a preferred embodiment of the invention, the lower segment that is substantially straight and the segment peak point-hollow point follow in succession, in particular are joined at the peak point forming a bend.

Preferably, the hollow point is different from the upper point and the line upper point-hollow point forms an angle with the line peak point-hollow point.

In particular, the line upper point-hollow point is vertical.

According to another embodiment the line upper point-hollow point is inclined in relation to the vertical.

According to a preferred embodiment the curve has a straight section which extends between the upper point and the hollow point, in particular from the upper point up to the hollow point.

According to a preferred embodiment the curve has a substantially straight segment, in particular a straight line, which extends between the peak point and the hollow point, in particular from the peak point to the hollow point.

According to a preferred embodiment of the invention the section of the curve which extends between the peak point and the hollow point comprises a turning point.

According to a preferred embodiment of the invention, the peak point is located at a level relative to the lower face of the layer which corresponds to at least 80% of the total height or thickness of the layer, as measured along the vertical line passing through this point.

Thus, the rigid part forms above the bending point or the bending area a kind of thin tab above the elastic part, the smallest thickness of which corresponds to at least 20% of the thickness of the layer.

In this way a junction is formed between the rigid part and the elastic part in the layer, which ensures excellent resistant of the join between the rigid part and elastic part of the layer, in particular high resistance to the stresses it may be subjected to, in particular when the laminate is stretched, for example when it is integrated into a nappy, in particular at the closure of the nappy on the waistband, for example when it is integrated into a flap in the form of a tab that can comprise hooks attached to a central part of the waistband and comprises loops for connecting with the hooks to close the nappy.

According to a preferred embodiment of the invention the total dimension in width (in direction CD) of the rigid part which extends above the elastic part is smaller than the width of the elastic part.

According to a preferred embodiment of the invention the layer comprises two rigid parts on either side of the elastic part and the two parts form respective thin tabs of the two rigid parts each extending above the elastic part while remaining apart from one another at their end.

According to a particularly preferred embodiment of the invention the two respective thin tabs of the two rigid parts on either side of the elastic part join together at their end following an interface of the tab.

By way of example a preferred embodiment of the invention is now described with reference to the drawings, in which.

Figure 14:
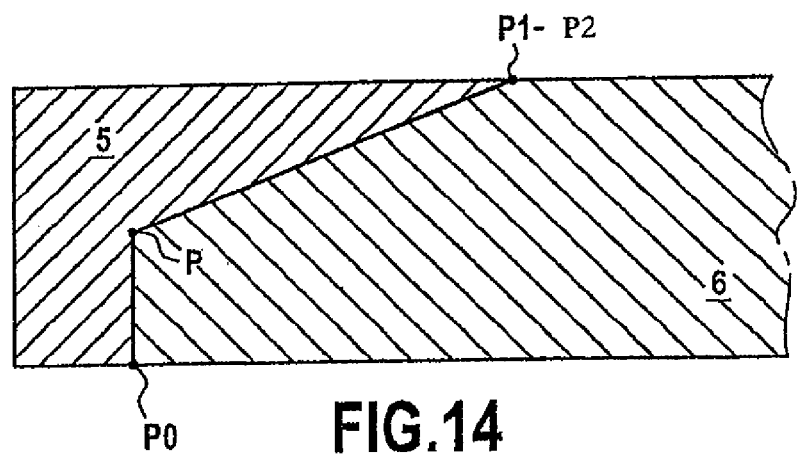
Figure 15:
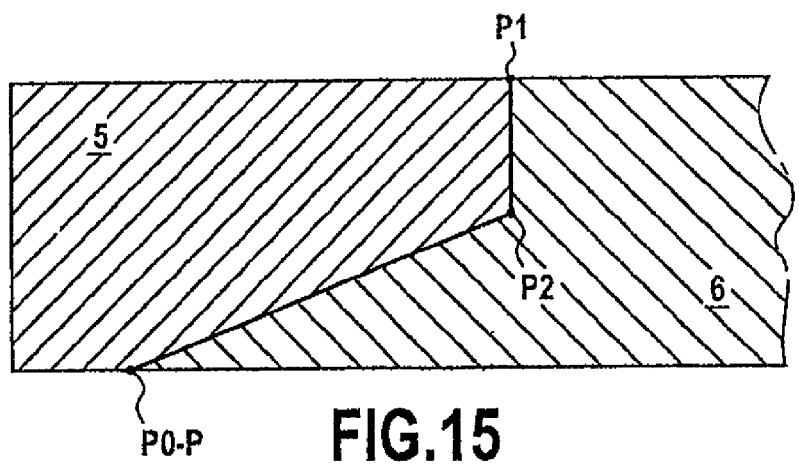
Figure 16:
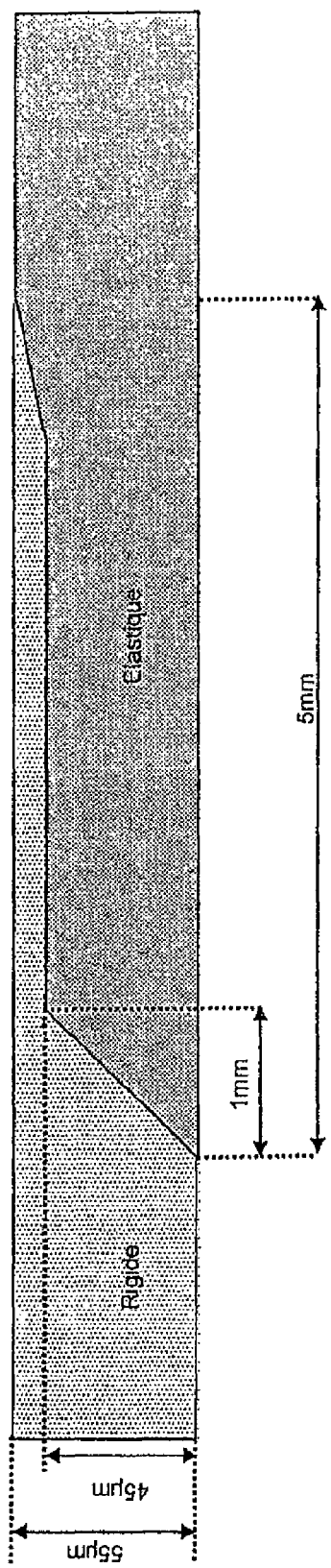

FIGS. 10 to 15 each shown another embodiment of a layer according to the invention; and FIG. 16 is an image of a cross section of a laminate according to the invention.

Figure 1:
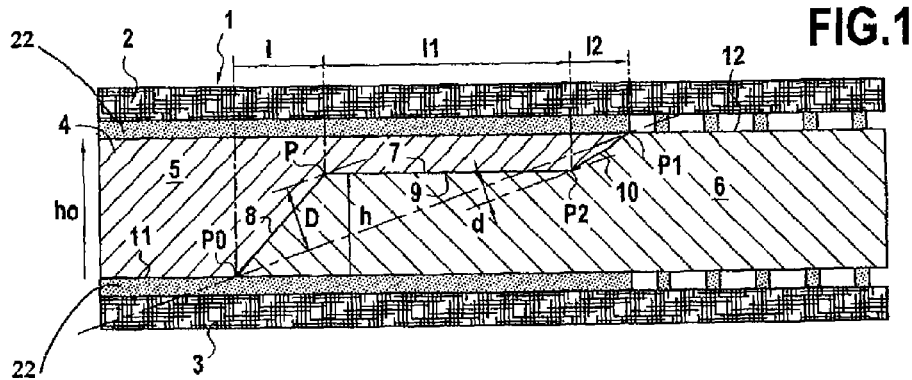
FIG. 1 is a cross-section CD, in a transverse plane relative to the direction of the machine (MD) and comprising direction CD and the vertical direction of a laminate according to the invention.
Figure 2:
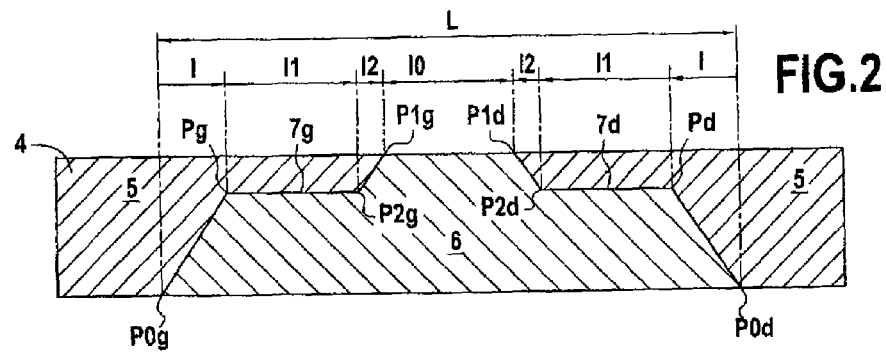
FIG. 2 is a cross-section of another embodiment of a laminate according to the invention.

FIG. 1 shows a laminate 1 comprising a non-woven upper layer 2, a lower non-woven layer 3 and an intermediate layer 4 sandwiched between the two non-woven layers. This layer 4 comprises a rigid part 5 and an elastic part 6. The laminate continues to the right, and in particular either in an identical form or further comprising another part 5 as shown in FIG. 2.

Part 5 is defined as being rigid as it is less elastic than the elastic part. The layer 4 is formed by the coextrusion of two films corresponding to the respective parts 5 and 6. The coextrusion of the two films for the formation of the layer 6 is controlled so that an interface is formed between the latter defined by a curve 7.

Said curve 7 comprises a first straight segment 8 coming from the lower face 11 of the layer, followed by a second straight segment 9, followed by the a third straight end segment 10. The first straight segment 8 extends from point P0 of the lower face 11 of the layer in the direction of the elastic part 6 up to a peak point P (here the peak point P is distinct from the lower point P0).

Point P is the point located, from the side of the diagonal where the rigid film 5 is located, the greatest distance from the diagonal line P0P1 as measured perpendicularly to the diagonal line P0P1.

This straight segment 8 is inclined at an angle of 30° to the vertical direction. From the peak point P, curve 7 comprises the second straight segment 9. This segment 9 is inclined in relation to the vertical direction by an angle greater than the angle by which segment 8 is inclined relative to the vertical and in particular by an angle of 90°, as in FIG. 1. However, this angle need not be 90°, but can be less than 90°, for example between 70 and 80°.

The intermediate segment 9 extends from the peak point P to a hollow point P2 which is the point of the curve from the side of the diagonal where the elastic film 6 is located, the greatest distance from the diagonal line P0P1 as measured perpendicular to the diagonal line P0P1. In this embodiment, the hollow point P2 and the upper point P1 are different.

Thus, following the intermediate segment 9, the end segment 10 extends from the hollow point P2 to point P1 of the upper face 12 of the layer, over a width I2 in the horizontal direction.

Figure 12:
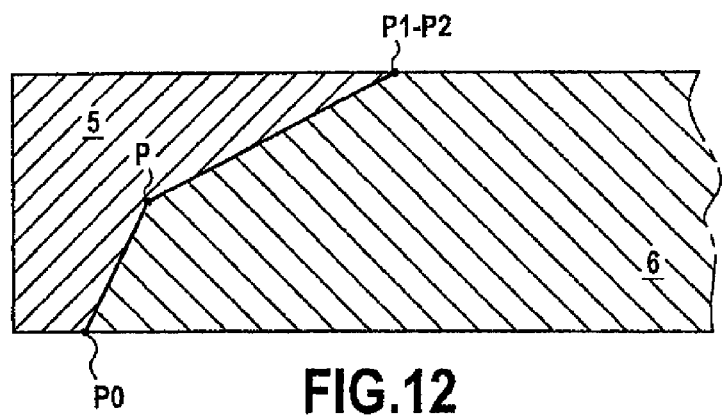

Instead of the two segments 9 and 10 it would be possible for example to have just one substantially straight segment which extends from point P to point P1, as shown in FIG. 12. In this case the upper point P1 and the hollow point P2 are merged, and the curve never passes the diagonal P0P1 from the side of the elastic film.

Figure 4:
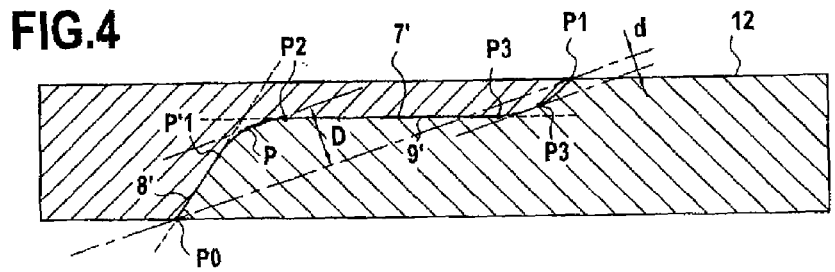
FIG. 4 is a further cross-section of another embodiment of a laminate according to the invention.

Furthermore, in reality or in microscopic detail it may be the case that the intermediate parts between segments 8, 9, 10 are not as straight as shown and in particular the intermediate parts between the straight segments 8 and 9 and between the straight segments 9 and 10 can be slightly curved as shown in FIG. 4. The curve may have for example a first substantially straight segment, for example 8' in FIG. 4, which extends to point P1' and a straight segment 9', which extends between point P2 and point P3. Between point P1' and point P2 of the curve 7' there is a curved segment. Likewise from point P3 to the upper surface 12 of the layer the curve 7' has a curved form. In the example of FIG. 4, to define point P the point at the largest distance D from the diagonal P0P1 and for point P2 the point at the farthest distance d from the diagonal from the elastic side.

The layer is fixed on either side to two non-woven layers 2 and 3, in particular as shown by the layers of glue 22, the layers of glue 22 being continued above and below the rigid part 5 and in the form of points or discontinuous lines above and below the elastic part. Thus, once the laminate is activated, i.e. stretched for the first time, for example by passing it between two toothed rollers, the non-woven materials are stretched and then relaxed and can thus follow the elasticity of part 6. Also according to another possibility, it is possible to use stretchable non-woven materials which do not need to be activated and which can also follow the elasticity of the elastic 6 to ensure the elasticity of the laminate 1 as a whole.

Point P is located at a height h which corresponds to at least 80% of the total height h0 or thickness of the layer. In particular, h can be between 80 and 95% of the height h0. Thus, above the elastic film 6 at the level of the second straight intermediate segment 9 a tab is formed made of less elastic or rigid material which is very thin (between less than 20% and 5%, or less, of the total thickness of the layer). This tab part is more extended than the wedge part corresponding to the straight segment 8. In particular, the width I1 over which the intermediate straight segment 9 extends is greater than the width I over which the straight segment 8 extends in horizontal direction and in particular is about three to five times greater.

According to an embodiment shown in FIG. 1, the layer of glue is continuous between the or each non-woven material and the rigid part up to point P1 at the top and bottom, in particular as shown in FIG. 1, up to a little beyond point P1. It is then discontinuous above and below the elastic part. According to another possible embodiment it is possible that the layer of glue is continuous up to point P0 then discontinuous from point P0 at the top and bottom over the whole width where the elastic part 6 is located.

It is also possible to provide the upper and lower layers of glue continuously up to a point between P and P1, in particular up to P1. It is also possible to extend the glue at the top and bottom to different levels, for example above or up to slightly beyond point P1 and below or down to a shorter distance, for example up to before P1, or up to P0 or even before P0.

FIG. 2 shows another embodiment in which two parts 5 are located on either side of the elastic part 6 of the layer 4. The two respective curves 7g and 7d (g and d for left and right) have substantially identical forms but are inverted relative to one another like a mirror. The two points P1g and P1d are spaced apart from one another on the upper face 12 by a distance 10.

Figure 3:
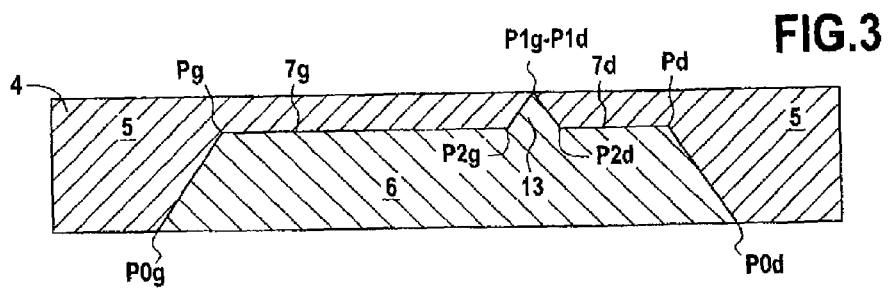
FIG. 3 is a further cross-section of another embodiment of a laminate according to the invention.

According to a preferred embodiment of the invention, the two points P1g and P1d as shown in FIG. 3 merge and the two tabs join together at an interface 13. Preferably, as shown, one of the tabs (the left one in the example of FIG. 3) extends over a greater horizontal distance than the other tab (the right one in the example of FIG. 3).

Figure 10:
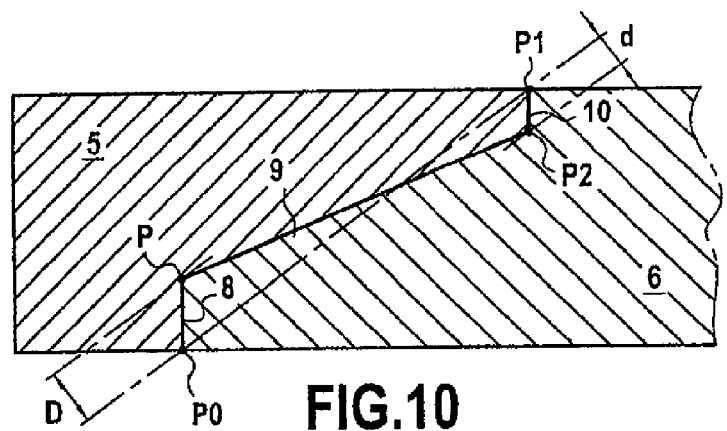

FIG. 10 shows an embodiment comprising a lower vertical segment which extends from the lower face to peak point P, followed by a straight intermediate segment between the peak point P and hollow point P2 inclined relative to the vertical and relative to the horizontal. Finally, an upper vertical segment extends from the hollow point P2 to the upper face P1.

Figure 11:
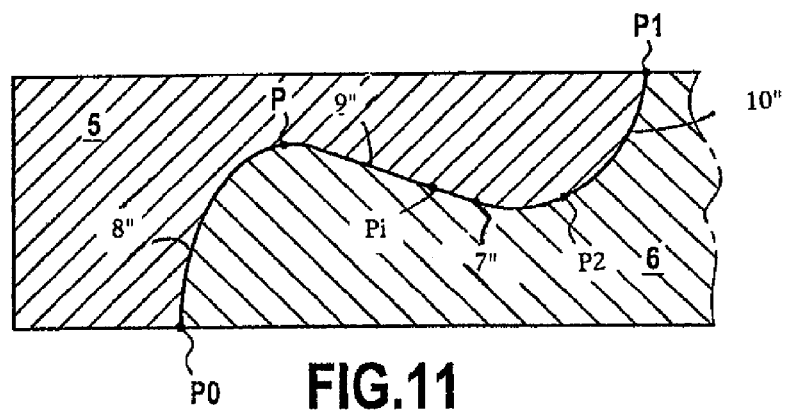

FIG. 11 shows an example without a straight segment. From the lower face P0 and to point P the curve 7'' has a curved section 8'', the concavity of which is turned towards the diagonal P0P1, the line P0P being inclined relative to the vertical. Likewise, the curve comprises between the upper face P1 and the hollow point P2 a curved section 10'' the concavity of which is turned towards the diagonal P0P1q, the line P1P2 being inclined relative to the vertical. Between the peak point P and the hollow point P2 the curve 7' has a curved section 9'' with a bending point Pi. The line PP2 is inclined relative to the vertical and the horizontal.

FIG. 12 shows an embodiment in which point P1 and the hollow point P2 are merged and points P0 and P are distinct, such that the line P0P exists but line P1P2 does not exist (i.e. it is formed by a single point). The curve 7 is formed in this case by a straight segment 8 which corresponds to P0P followed by segment 9 which corresponds to PP1 or PP2. The two segments form an angle between then and are each inclined relative to the vertical and the horizontal, i.e. the P0P is inclined relative to the vertical and PP2 is inclined relative to the horizontal.

Figure 13:
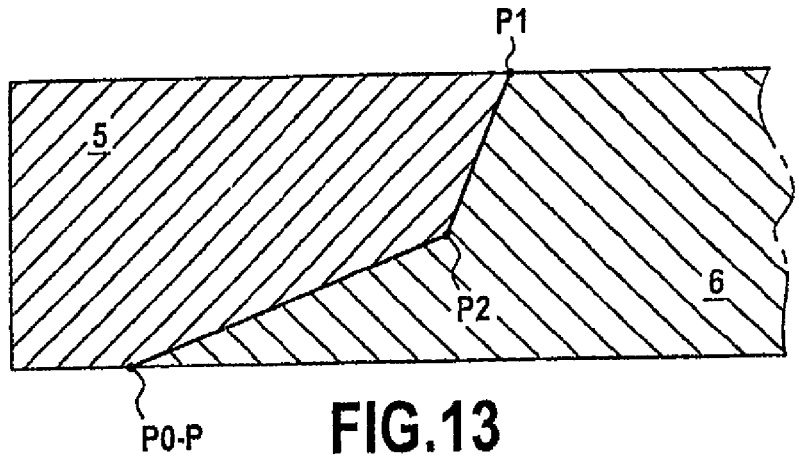

FIG. 13 shows an embodiment in which point P0 and the hollow point P are merged and point P1 and P2 are distinct, such that line P1P2 exists but line P0P does not exist (i.e. it is formed by a single point). The curve 7 is formed in this case by a straight segment 9 which corresponds to P0P2 followed by segment 10 which corresponds to P1P2. The two segments form an angle between them and are each inclined relative to the horizontal and vertical, that is P0P2 is inclined relative to the horizontal and P1P2 is inclined relative to the vertical.

FIG. 14 shows an embodiment in which point P1 and the hollow point P2 are merged and point P0 and P are distinct, such that the line P0P exists but line P1P2 does not exist (i.e. it is formed by a single point). The curve 7 is formed in this case by a straight segment 8 which corresponds to a P0P followed by segment 9 which corresponds to PP1 or PP2. The two segments form an angle between them. P0P is vertical and PP1 or PP2 is inclined relative to the horizontal.

FIG. 15 shows an embodiment in which point P0 and the hollow point P are merged and point P1 and P2 are distinct, such that the line P1P2 exists but line P0P does not exist (i.e. it is only formed by a single point). The curve 7 is formed in this case by a straight segment 9 which corresponds to P0P2 followed by segment 10 which corresponds to P1P2. The two segments form an angle between them. P0P2 is inclined to the horizontal and P1P2 is vertical.

Figure 8:
FIG. 8 shows a transverse cross section of another embodiment of the layer after forming by extrusion and before being assembled in one or two non-woven layers.

As can be seen by way of the example in FIG. 8, the thickness of the layer measured in a direction vertical to the figure, i.e. perpendicular to the direction in width and the direction in length of scrolling is substantially constant over the transverse extension of each elastic area or reinforcing area. However, as can be seen in the same FIG. 8, it may be the case that the thickness of the elastic areas varies in an increasing then decreasing manner passing a maximum between its two junctions with the areas of reinforcement, but the thicknesses of the elastic film or films and of the area or areas of reinforcement are such that at their respective junction the upper and/or lower surfaces of the layer are substantially without any roughness or discontinuity.

Thus for example, the elastic film or films have a grammage of about 10 to 40%, preferably 10 to 25% greater than that of the reinforcing film or films, the elastic film or films having for example a grammage of 55 g/m$^2$ whereas the reinforcing film or films have a grammage of 45 g/m$^2$.

At the joining or connecting section which extends over a width in general between 3 and 10 mm, in particular 5 mm, the thickness of each film (reinforcing and elastic) is lower than the thickness of the film outside the join. Thus each film of the join comprises a part with a smallest thickness which is assembled by superpositioning on the part of smallest thickness of the other film of the join.

In the present invention, by film or elastic area in a given direction a film or an area is extended which returns to its initial form after having been stretched or elongated in the given direction, at ambient temperature. Preferably, it is a film or an area which only has a small residual deformation or remanence after deformation and relaxation (permanent set or SET), namely less than 10%, more preferably less than 5% of the initial length, for an elongation of 100% of the initial length of the specimen at ambient temperature (T≈23° C.).

More preferably, the elastic film is able to withstand an elongation to break of at least 300% at ambient temperature and, preferably, an elongation of at least 600%, and more preferably at least 1,000%, at ambient temperature and at a stretching speed of 508 mm/min. The material from which the elastic film can be made is either a pure elastomer, or mixtures with an elastomeric phase or a material which always has substantially elastomeric properties at ambient temperature, such as for example polyolefins made by a metallocene type catalysis. It can also comprise a charge of thermoplastic material to assist with the formation of the layer as a single piece with reinforcing films.

To measure the remanence or SET of a specimen and therefore determine whether it is the specimen of an element, in particular an elastic film, the following method is used:

The specimen is conditioned in normal atmosphere, as defined by the standard ASTDM 5170, temperature of 23° C.±2° and relative humidity of 50%±5%.

A dynamometer is used as the apparatus corresponding to the standard EN 10002, in particular Synergie 200H, 1 column available from the company MTS Systems Corp, USA, conjointly with the user software TESTWORKS 4.04 B.

The specimen is prepared by cutting the product whose elasticity is to be measured with a hollow punch into a specimen with a rectangular shape (for example 45 mm wide in direction MD (direction of the machine, perpendicular to the plane of FIG. 1) and a length in direction CD (transverse direction, horizontal direction in FIG. 1) of 60 mm.

Figure 6:
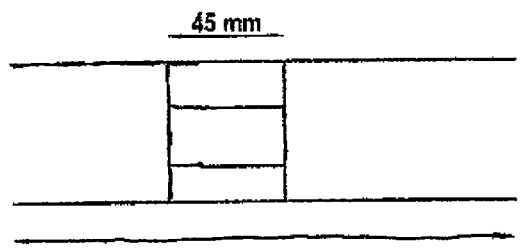
FIG. 6 is a diagram representing a sample of elastic or elastomeric material prepared to determine the SET.

The specimen is positioned between the jaws on either side of the area for which the elasticity is to be tested and from each side as shown schematically in FIG. 6.

The parameters are selected as follows:
distance between the jaws: 20 mm
machine speed: 254 mm/min
number of cycles: 2
elongation of the product: 100% at constant speed.

Figure 7:
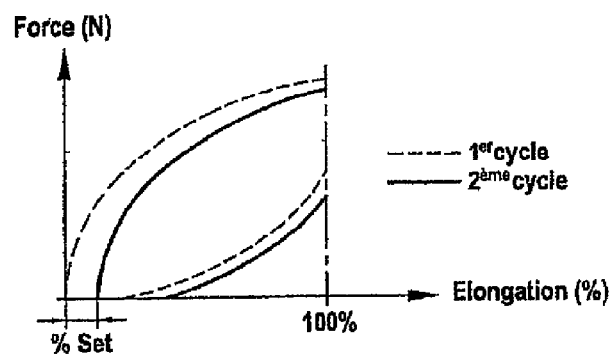
FIG. 7 shows the shape of the hysteresis curve obtained during the determination of the SET of the material, in particular an elastic or elastomeric material.

The product is stretched 100% by vertical displacement of the jaws, after the application of a precharge of in the order of 0.05 N, then it is held in position for 30 seconds (first cycle), then it is allowed to return to its initial position in which it is left for 60 seconds, then it stretched again by 100%, it is held for 30 seconds (second cycle) and returns to its initial position. Then the curve is obtained providing the stretching force in N as a function of the extension in %, having a hysteresis which can then be characterised by the SET (n=2), namely the point of the starting curve of the second cycle which intersects the x axis (elongation in %) in FIG. 7.

More preferably, the elastic film is able to withstand an elongation to break of at least 300% at ambient temperature, preferably an elongation of at least 600%, and more preferably at least 1,000%, at ambient temperature and at a stretching speed of 508 mm/min. The material from which the elastic film is made can either be a pure elastomer, or mixtures with an elastomeric phase or material that always has properties that are substantially elastomeric at ambient temperature, such as for example polyolefins from metallocene type catalysis. It can also comprise a charge of thermoplastic material to assist with the formation of the layer in one piece with the reinforcing films.

The material of the elastic film, in particular elastomeric film, can be a heat-shrinkable or non-heat-shrinkable elastic material. It can be formed, in particular, from polymers, such as copolymers with different types of patterns of monomers, for example alternated such as A-B, or sequenced for example A-A-A-B-B-B, or statistic, for example A-A-B-A-B-B-A-A-A-B-A, the whole of the network obtained can have different structures, either linear ones of the type A-B-A, or radial ones of the type A-B, index n (n>2) or diblock of the type A-B which are elastomeric, for example the copolymers styrene/isoprene (SI), styrene/isoprene/styrene (SIS), styrene/butadiene/styrene (SBS), styrene-ethylene/butylene-styrene (SEBS), styrene-ethylene/propylene-styrene (SEPS) or SIBS. Mixtures of these elastomers with one another or with non-elastomers modifying characteristics other than elasticity can also be considered. For example up to 50% by weight but, preferably, less than 30% by weight of polymer can be added as a stiffening agent, such as styrene polyvinyls, polystyrenes or poly-α-methyl styrene, epoxy polyesters, polyolefins for example of polyethylenes or certain ethylene/vinyl acetates, preferably those of increased molecular weight.

The material of the elastic film may be in particular a styrene-isoprene-styrene, available for example from the company Kraton Polymers, with the name KRATON D (registered trade mark) or the company DEXCO POLYMERS LP with the name VECTOR SBC 4211 (registered trade mark). It is also possible to use a thermoplastic elastomer of polyurethane, in particular PELLATHANE (registered trade mark) 2102-75A of the company The Dow Chemical Company. It is also possible to use a styrene-butadiene-styrene, in particular KRATON D-2122 (registered trade mark) of the company Kraton Polymers or the VECTOR SBC 4461 (registered trade mark) of the company Dexco Polymers LP. It is also possible to use a styrene-ethylene/butylene, in particular KRATON G-2832 (registered trade mark) of the company Kraton Polymers or a sequenced copolymer styrene-ethylene-butylene-styrene (SEBS), in particular KRATON (registered trade mark) G2703. It is also possible to use a copolymer of isooctyl acrylate and acrylic acid according to the monomer ratios 90/10. It is also possible to use a sequenced copolymer polyether polyamide PECAX (registered trade mark) 2533 of the company Arkema.

Other possible materials are polyolefin polymers with the characteristics of elastomers, in particular made from the metallocene catalysis, such as VISTAMAXX VM-1120 (registered trade mark), available from the company Exxon Mobil Chemical or EPDM charged polymers of Santoprene.

If glue is used as an adhesive for fixing elastic films and thermoplastic films to non-woven layers and possibly gluing together non-woven layers, it is possible according to the invention to use a glue such as a hot melt non-reactive glue, for example H2511 from Bostik, or a reactive glue, in particular AX75E from Bostik or reactive PU glues.

Preferably, these glues will have a similar compatible chemical nature as or be compatible with the material forming the elastic film and/or thermoplastic film or reinforcing film described above.

With regard to the non-woven layers it is possible to use non-woven layers that are spunbond and/or meltblown and/or card calendered and/or spunlace and as a base material comprises one or more polyolefins, preferably polypropylene, polyester or a mixture of the latter. In particular, the non-woven "spunbond" layer is based on long fibres or filaments, with a titre in dTex (mass in grams divided by a length of 10,000 m thread) between 1 dTex and 6 dTex, for example 2.2 dTex. In particular, if the laminate comprises two layers of non-woven material, the layers may be different types and/or made of different materials.

Preferably, the or at least one of the non-woven materials or the two non-woven materials has/have a grammage of between 5 and 25 g/m$^2$, in particular between 5 and 15 g/m$^2$, more particularly between 5 and 10 g/m$^2$.

In particular, if the non-woven material is a material which does not have the ability to stretch itself and has to be activated, the grammage is between 5 and 20 g/m$^2$, in particular is about 15 g/m$^2$ for a spunbond or about 8 g/m$^2$ for a meltblown material. If the non-woven material does not need to be activated for the laminate to have elastic capacity, that is if the non-woven material can stretch itself over an elongation range by at least 50%, preferably at least 100%, the grammage is preferably between 15 and 25 g/m², for example it is 22 g/m² for a card calendered material or 25 g/m² for a spunlace material. Furthermore, it should be noted that the two non-woven materials, if there are two of them, can be different from one another.

In order to determine whether an element, in particular a film, is more extendable than another element, for example another film, according to the invention, it is possible to use an elongation at break test as follows:

A dynamometer according to the standard EN 10002 is used as the apparatus, for example the same as for the elasticity test above, namely the Synergie 200H, 1 column, available from the company MTS Systems Corp, USA, together with the user software TESTWORKS 4.04 B. A specimen is prepared in a rectangular shape, for example 45 mm wide and 60 mm long. The specimen is positioned between the jaws on either side of the area to be tested for elongation and from each side as shown in FIG. 6 schematically.

The parameters are selected as follows:
distance between the jaws: 20 mm
machine speed: 254 mm/min
elongation of the product: up to break at constant speed.

Figure 9:
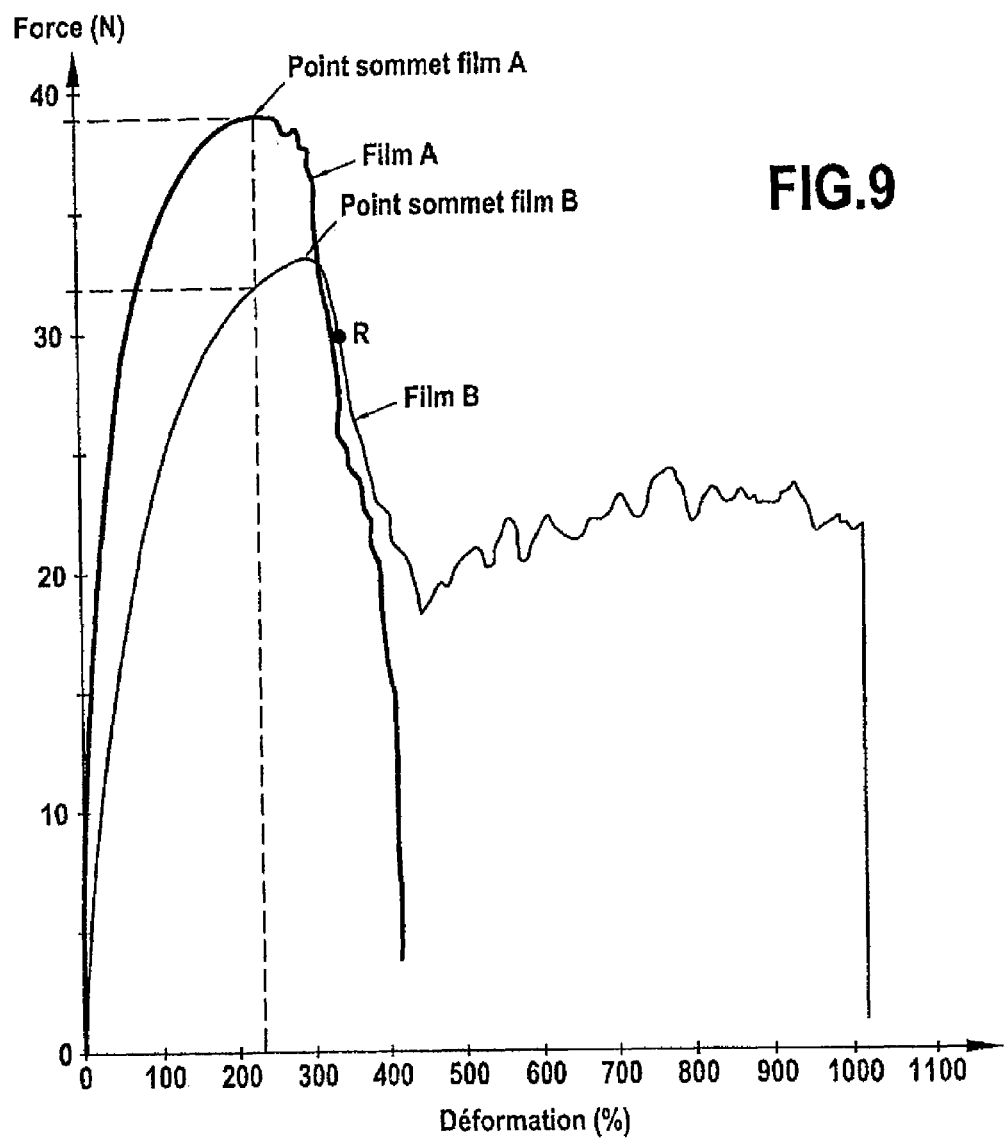
FIG. 9 shows examples of curves showing stretching as a function of force for testing the relative stretching capacity.

After applying a precharge of 0.05 N, the product is extended to break by the vertical displacement of the jaws. In this way for each specimen a characteristic curve is obtained giving the stretching force in N as a function of the elongation in %, as shown in FIG. 9. Each curve has a peak point, from which the elongation increases with decreasing force. This peak corresponds to the transitional point of the element towards destruction.

In order to determine which of the two elements, in particular of the two films, is less extendable, the above method is used to test the two elements, in particular the two films, in order to obtain their respective characteristic curve. Each curve has a given peak point to which a given respective elongation corresponds. As the reference elongation the smallest of the two given elongations of the two curves is selected or the given elongation if the two given elongations are identical and for said given smallest elongation the two stretching forces of each curve are compared and the element having the greatest stretching force for this reference elongation is the less stretchable element. Thus for example in FIG. 9 the reference elongation is the elongation corresponding to the peak point of film A, namely about 240% and at this reference elongation, the curve of the film A gives a stretching force of about 40 N and the curve of film B a stretching force of about 32.5 N, such that film A is the least stretchable.

With regard to the material of the reinforcing bands, it is possible to select a material or a mixture of several materials such as those of the thermoplastic family, for example polyethylene, polypropylene, polyester or any similar material, as well as materials from the family of thermoplastic elastomers used for the elastic film, (however of the sort that the reinforcing film in any case has less elongation than the elastic film), which makes it possible to ensure good compatibility of the materials forming the layer in one piece. Preferably, a thermoplastic material is selected with good compatibility to the elastic or elastomeric material of the elastic film so that the connection between them along their respective edge, after cooling, is the strongest possible. Specific examples of material for reinforcing films are the polyethylene Riblene MV 10 (registered trade mark) of the company Polimeri Europa, or MG 9621 of the company Borealis, or LD 259 or LD 655 of the company Exxon Mobil Chemical.

Figure 5:
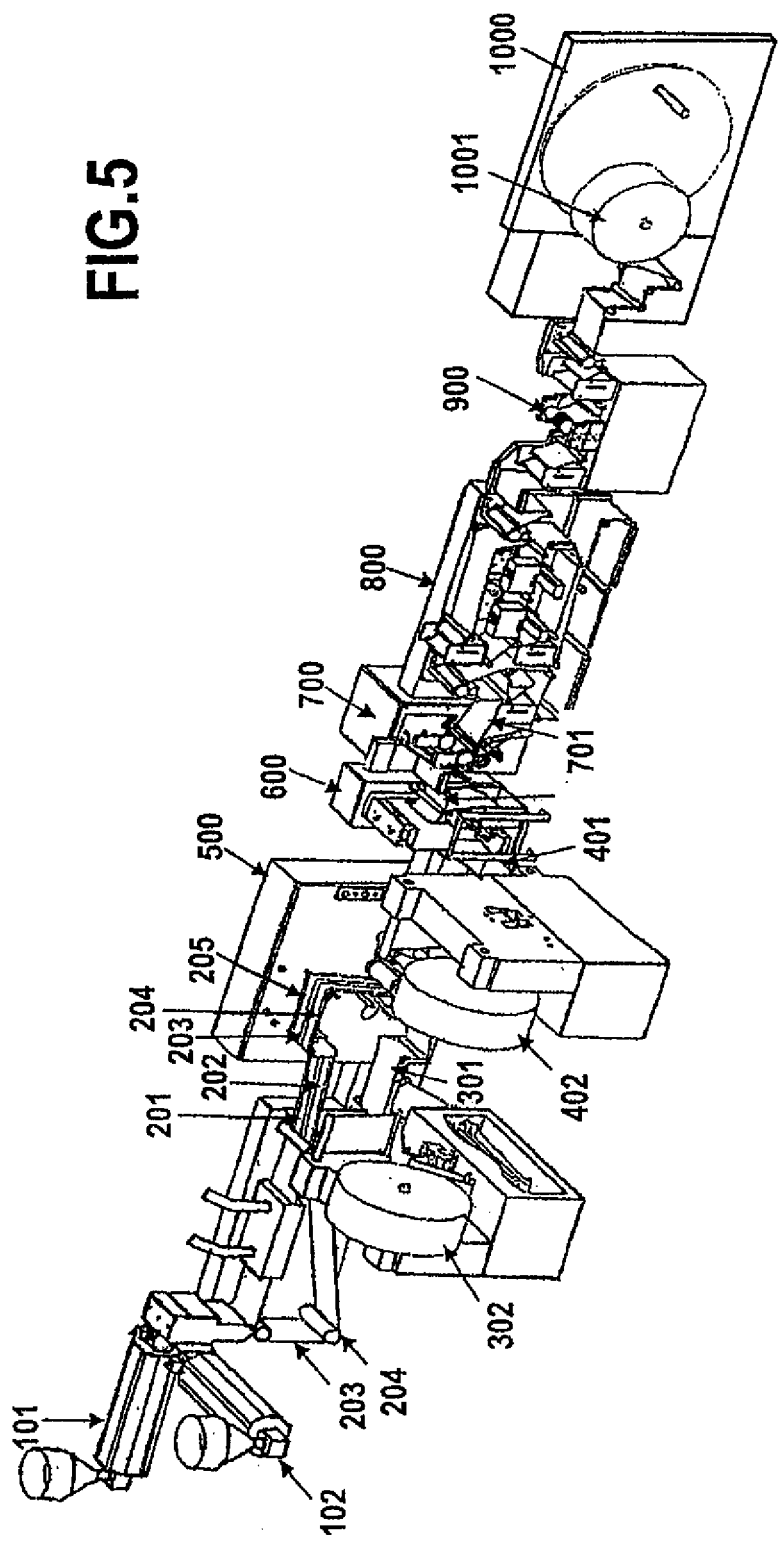
FIG. 5 is a perspective view of a production installation of a laminate according to the invention, in particular laminates of the preceding figures.

FIG. 5 shows an installation for the production of a laminate according to the invention: the installation comprises an extruder 101 which forms by extrusions two bands 201, 202 of elastic films which by means of belt systems 203 and rollers 204 are transported between two rollers at the same time as two layers of non-woven material 301 and 401 to be fixed by cooling the elastomeric material between the non-woven material in a fixing unit 500. The non-woven material 301 is unwound from a bobbin 302. The second non-woven fabric 401 is unwound from a bobbin 402. The extruder 102 also produces three bands 203, 204, 205 of thermoplastic material. The five bands 201 to 205 are coextruded next to one another having contiguous edges, such that at the outlet of the coextruder and then after cooling they form a single piece. The complex formed by the non-woven materials 301 and 401 and the elastic and thermoplastic bands 201 to 205, namely complex 601, is then laminated in a calender 600, cut to the right width in a cutting unit 700 comprising circular blades 701, then passes into a soldering unit 800 for soldering the longitudinal edges. The non-woven materials are then activated by defibrillation in an activation unit 900.

At the outlet of the activation unit 900 the laminate as a whole is wound onto a winder 1000 in a roll 1001 which can then be taken directly to units for the production of nappies for inserting into a nappy.

Preferably, the elastic or elastomeric film or films have a thickness of between 20 microns and 120 microns. Likewise, the reinforcing bands preferably have the same thickness.

According to the application it is possible to select the dimensions of reinforcing films of thermoplastic material such that one of them extends exactly up to one of the left or right edges of the laminate, whereas at the other edge either the band extends also up to the right or left edge exactly, or projects a small distance beyond the edge of the laminate, or ends back from the edge so as to form a small border, in particular without a reinforcing film.

In particular, to obtain the desired form of interface curve, also on the form of the tooling, it is possible to play on the relative viscosities of the materials used in the formation of the rigid part and elastic part, which will have an effect on the intrinsic respective forces of the two material in competition during the formation of the join. Thus with identical tooling the lower the relative viscosity of the material of the elastic part relative to the material of the rigid part, the more the rigid part superposed on the elastic part will have a small thickness.

In order to achieve this objective a material is used for example with a viscosity of the elastic part that is 20 to 50% lower than that of the rigid part, such as for example a material of MFR 3.15 g/10 mn for the elastic part and a material of MFR 4.60 g/10 mn for the rigid part, MFR being measured according to the standard NF EN ISO 1133 at 190° and 2.16 kg.

The angle at which the first straight segment is inclined relative to the vertical may be in particular between 5 and 60°, preferably between 15 and 45°, in particular between 25 and 40°.

The angle between the vertical and the second segment may be between 30° and 90° (90° when it is horizontal), in particular between 60° and 90°, more preferably between 75° and 90°.

In the present invention the laminate is described by defining a lower face and an upper face. However, it should be noted that this is carried out with the sole aim of simplifying the description and the terms lower and upper are used in connection with the figures and in reality their relative position (top and bottom) can be inversed without departing from the scope of protection of the invention. Another more precise but complex way of defining things might have been to mention a face and an opposite face.

FIG. 15 shows an image of a transverse cross-section of a laminate according to the invention, in particular corresponding to FIG. 1. The join is indicated by a line of connected points.

The invention claimed is:

1. Laminate comprising a stack, in a vertical direction, of at least one non-woven layer and a layer made in one part or as an integral part attached to the at least one non-woven layer, in particular by means of an adhesive, the layer comprising a first face or lower face and a second face or upper face between which at least one elastic section in the form of a film extends and at least one rigid section in the form of a film made from a less elastic material than the material of the elastic section, in particular a section made from a non-elastic material, the layer being obtained by coextrusion of the at least two elastic and rigid films, such that an interface is formed between them, characterized in that, as viewed in cross section, the curve or line formed by the interface between the two films extends from a point (P0) of the lower face to a point (P1) of the upper face mutually offset in horizontal direction, the diagonal line passing through these two points being inclined in relation to the vertical of the layer;

a peak point (P) of the curve from the side of the rigid film is defined as the point most remote from the diagonal line from the side of the rigid film, the distance from the diagonal line being measured perpendicular to the latter, the peak point being merged with the point of the lower face in cases where the curve does not exceed the diagonal from the side of the rigid film and a hollow point (P2) of the curve from the side of the elastic film is defined as being the point that is most remote from the diagonal line from the side of the elastic film, the distance to the diagonal line being measured perpendicular to the latter, the hollow point being merged with the point of the upper face in cases where the curve does not exceed the diagonal from the side of the elastic film;

at least one of the peak and hollow points being different respectively from the lower and upper points;

the line passing through the point of the lower face and the peak point and/or the line passing through the point of the upper face and the hollow point forms an angle with the line passing through the hollow point and the peak point; and at least one out of the line (P0P) lower point-peak point, the line (PP2) peak point-hollow point and line (P2P1) hollow point-upper point is inclined respectively in relation to the vertical direction, in relation to the horizontal direction and in relation to the vertical direction.

2. Laminate according to claim 1, characterized in that the lower point and the peak point are different, the line lower point-peak point is inclined in relation to the vertical and the line hollow point-peak point is substantially horizontal.

3. Laminate according to claim 1, characterized in that the lower point and the peak point are different, the line lower point-peak point is substantially vertical and the line peak point-hollow point is inclined in relation to the horizontal.

4. Laminate according to claim 1, characterized in that the lower point and the peak point are different, the line lower point-peak point is inclined in relation to the vertical and the line peak point-hollow point is inclined in relation to the horizontal.

5. Laminate according to claim 1, characterized in the curve (7, 7') comprises between the lower face and the peak point a lower segment (8, 8') that is substantially straight, in particular is straight.

6. Laminate according to claim 1, characterized in that the curve (7, 7') comprises an intermediate segment (9, 9') which extends from the peak point to the hollow point.

7. Laminate according to claim 1, characterized in that the extension in horizontal direction of the line lower point-peak point is smaller than the extension in horizontal direction of the line peak point-hollow point.

8. Laminate according to claim 1, characterized in that the hollow point is distinct from the upper point and the line upper point-hollow point forms an angle with the line peak point-hollow point.

9. Laminate according to claim 8, characterized in that the curve has a straight segment which extends between the upper point and the hollow point, in particular from the upper point to the hollow point.

10. Laminate according to claim 1 characterized in that the peak point is located at a level relative to the lower face of the layer which corresponds to at least 80% of the total height or thickness of the layer, as measured along the vertical line passing through this point.

* * * * *